United States Patent [19]

Harris et al.

[11] Patent Number: 4,827,059
[45] Date of Patent: May 2, 1989

[54] DICHLOROBUTENE ISOMERIZATION PROCESS

[75] Inventors: Alexander T. Harris, Metairie; Donald A. Melchert, Jr., Kenner, both of La.

[73] Assignee: E. I. Du Pont de Nemours and Company, Wilmington, Del.

[21] Appl. No.: 216,422

[22] Filed: Jul. 8, 1988

Related U.S. Application Data

[63] Continuation-in-part of Ser. No. 130,281, Dec. 8, 1987, abandoned.

[51] Int. Cl.$^4$ .............................................. C07C 17/24
[52] U.S. Cl. .................................... 570/236; 570/104
[58] Field of Search ................................ 570/236, 104

[56] References Cited

U.S. PATENT DOCUMENTS 3,819,730  6/1974  Nakata et al. ........................ 570/236

FOREIGN PATENT DOCUMENTS 723185  12/1965  Canada ................................ 570/236

Primary Examiner—Howard T. Mars

[57] ABSTRACT

Formation of solid and/or high boiling residues during the isomerization of one of 1,4-dichlorobutene-2 and 3,4-dichlorobutene-1 into each other in the presence of a cuprous chloride catalyst is inhibited by the addition to the isomerization reaction of a small amount of a hydroxylamine salt.

13 Claims, No Drawings

DICHLOROBUTENE ISOMERIZATION PROCESS

CROSS-REFERENCE TO RELATED APPLICATION

This is a continuationa-in-part of our application Ser. No. 130,281, filed Dec. 8, 1987.

BACKGROUND OF THE INVENTION

This invention relates to an improved process for the isomerization of dichlorobutenes, wherein formation of solids and high boiling byproducts is inhibited.

It is known to isomerize 1,4-dichlorobutene-2 to 3,4-dichlorobutene-1, or vice versa, in the presence of a copper salt, e.g., in the presence of a complex of a copper salt with a quaternary ammonium compound, as described in U.S. Pat. No. 3,819,730 to Nakata et al. 1,4-Dichlorobutene-2 is a valuable intermediate in the manufacture of certain important polyamides, such as nylon 66; while 3,4-dichlorobutene-1 is an equally valuable intermediate in the manufacture of chloroprene, which is the basic monomer in the manufacture of a class of important synthetic rubbers known as the neoprenes. In the Nakata et al. process, substantially pure 1,4-dichlorobutene-2 or 3,4-dichlorobutene-1, or a mixture thereof is fed to a constant boiling reactor operating under reduced pressure and containing the cuprous chloride/quaternary ammonium compound catalyst; the isomerized dichlorobutene compound is taken off as a vapor, then condensed and fractionated to yield substantially pure 3,4- and 1,4-dichlorobutene, respectively. There are known other processes based on a cuprous compound catalyst or complexes of cuprous chloride with amines, amides, or nitriles.

The above processes suffer to a greater or lesser degree from side reactions, which lead to the formation of high boiling liquids or of solids, likely containing oligomerized and/or polymerized materials, which eventually cause clogging of the reactor, reduce the efficiency of heat exchange in the reactor, and naturally reduce the yield of isomerized dichlorobutene.

It is, therefore, the objective of this invention to provide an improvement in the dichlorobutene isomerization process wherein those side reactions would be substantially inhibited.

SUMMARY OF THE INVENTION

According to this invention, there is provided in the process for the isomerization of one of 1,4-dichlorobutene-2 and 3,4-dichlorobutene-1 into the other by heating the dichlorobutene to be isomerized in the presence of a cuprous compound catalyst, in the bbsence of water, and with substantial exclusion of air at a temperature at which the system is homogeneous, and removing the isomerized product from the reaction medium, the improvement of having present during the isomerization in the reaction medium a hydroxylamine salt in an amount of about 0.05-0.6%, based on the weight of dichlorobutene to be isomerized.

DETAILED DESCRIPTION OF THE INVENTION

The isomerization process can be any known dichlorobutene isomerization process in which a cuprous salt is used as the catalyst, but preferably will be the process of the Nakata et al. patent, which is herein incorporated by reference, wherein the catalyst is a complex of a cuprous salt with a quaternary ammonium salt. The usual cuprous salt is cuprous chloride, although other salts such as, e.g., cuprous bromide or cuprous sulfate also can be used. If a complex with a quaternary ammonium salt is to be employed, many suitable quaternary ammonium salts can be represented by the formula $R_nR'_mR''_pNCl$, where R is an aryl or alkaryl radical or a chlorine substituted butenyl radical; R' is an alkyl radical of 1'3 carbon atoms; R'' is an alkyl radical having 4–18 carbon atoms; $n+m+p=4$; $n=0$ or 1; and each of m and p, independently, is 0 or an integer from 1 to 4. Typical quaternary ammonium salts suitable in this process include, e.g., butyltrimethylammonium chloride and quaternary ammonium salts derived from 1,4-dichlorobutene-2 and trimethylamine or triethylamine. It is preferred to operate with a catalyst complex in which the mole ratio of the quaternary ammonium salt to the cuprous salt is about 0.8. Greater ratios require more catalyst, and this increases the risk of equipment corrosion. Under the conditions of the Nakata et al. process, for the above indicated quaternary ammonium salt/cuprous salt mole ratio, the optimum results are obtained when the amount of catalyst is such that the amount of copper, calculated as cuprous chloride, is about 1.5% by weight of dichlorobutenes present in the reactor. Below 1.5%, the rate of isomerization may be too low for a commercially attractive operation, although successful isomerizations can be carried out even when the amount of catalyst is reduced to about 1% of copper, calculated as cuprous chloride; while above 2% severe corrosion problems may be encountered.

The isomerization reaction normally is carried out at a reduced pressure such that the reaction medium is at its boiling temperature, and the product can be removed therefrom. Normally, the pressure will be about 2.5–80 kPa and the temperature will be about 60°–150° C., preferably about 60°–120° C. at 2.5–28 kPa, especially about 90°–112° C. at 9.3–24 kPa.

The process can be run either batchwise or continuously, but it is naturally preferred to run it continuously. When operated in this manner in the plant, the process produces about 0.3–0.6%, based on the volume of dichlorobutenes in the reactor, of solid and/or high boiling residue per day. The process of this invention can be operated continuously for about 4–6 weeks until the amount of residual solids and high boilers reaches about 25–30% of the reaction medium and, from then on, is intermittently purged to maintain the level of that residue at about 25%. The process can thus be operated with intermittent purges for several months. In the absence of the inhibitor, the reactor must be purged after about two weeks of continuous operation.

The amount of hydroxylamine salt to be used in the process as inhibitor depends to some extent on the amount of air present in the system. Under ideal conditions, in the laboratory, air can be completely excluded, but in the plant it can be maintained at a controlled partial pressure. The process may also be operated under a nitrogen blanket. When there is no air in the system, the amount of inhibitor may be reduced below about 0.05%, but normally, at least under prevailing plant conditions, there will always be some air present, and the partial air presssure normally will be about 0.5 kPa. More than about 0.6% of hydroxylamine salt is not recommended because no additional benefits are realized, and the additional expense is unnecessary. The most commonplace and most practical hydroxylamine salt is hydroxylamine hydrochloride but other salts such as, e.g., hydroxylamine sulfate, bisulfate, hydrobromide, acetate, trichloroacetate etc. also can be used. Free hydroxylamine also can be used since a hydrochloride salt is formed in situ in the presence of hydrogen chloride, which always is evolved to a minor extent due to side reactions.

While hydroxylamine salts have been shown to have this inhibiting effect, and one might be tempted to conclude that it would be sufficient to merely have present in the reaction medium an antioxidant, other generally used antioxidants surprisingly do not have the same beneficial effect. For example, tert-butylcatechol, which is a well known industrial antioxidant, is not effective in this process because it gels the reactor charge within 24 hours, possibly due to a complex formation with the catalyst. Phenothiazine and pyrogallol both caused immediate gelling as the materials were being mixed at the beginning of the tests, and thus also were ineffective as inhibitors.

In order to determine the effectiveness of an inhibitor, one can determine the amount of residue either by gas chromatography or by evaporating dichlorobutenes at about 2.7 kPa and weighing the residue. The residue is thixotropic and forms a gel.

This invention is now illustrated by the following examples of certain preferred embodiments thereof, where all parts, proportions, and percentages are by weight, except that the amount of solid and/or high boiling residue is expressed as a volume percent of the total reactor content.

EXAMPLE 1

A catalyst solution was prepared in a 1 liter flask equipped with a stirrer and condenser under a nitrogen atmosphere by adding 7.2 g of triethylamine hydrochloride to 594 ml of 1,4-dichlorobutene at 54° C. The mixture was stirred for 1 hour, after which 8.9 g of cuprous chloride was added to form a soluble quaternary ammonium cuprochloride compound. A 4.0 g sample of hydroxylamine hydrochloride (0.6% by weight of dichlorobutene) was then added, and the mixture was heated to 100° C. and allowed to react for 22 days. Test samples consisting of 1.0 ml aliquots were removed daily commencing with the second day and these were analyzed by gas chromatography for % dichlorobutene, % high boilers, and % residue using a 3 mm o. d. stainless steel column packed with 5% polyethylene glycol (Carbowax ® 20M TPA, Union Carbide Corp.) on acid washed 60/80 mesh (0.246-0.175 mm) calcined diatomaceous earth (Chromsorb ® "P", Johns-Manville Corp.). The rate of formation of residue, as determined by this analysis, was 0.3% per day of the volume of the reactor converted to residue. The same analytical technique was used in all the subsequent examples.

COMPARATIVE EXAMPLE A

Using the same reactor and conditions as described in Example 1, a comparative experiment was performed using the same ingredients in the same amounts, except that no hydroxylamine hydrochloride inhibitor was present. After 3.7 days the measured residue formation rate was 1.2% per day of the volume of the reactor converted to residue.

EXAMPLE 2

A similar experiment was conducted using the same reactor and procedure as described in Example 1 with the same ingredients in the same amounts, except that an air sweep of 0.5 cm$^3$/min was introduced to the reactor. The reactor was operated for 6.75 days, and after that time the measured residue formation rate was 1.2% per day of the volume of the reactor converted to residue.

COMPARATIVE EXAMPLE B

Using the same reactor and conditions as described in Example 2, a comparative experiment was performed using the same ingredients in the same amounts, except that no hydroxylamine hydrochloride was present. After 2.9 days, the reaction mixture was completely gelled and the residue formation rate was greater than 20% per day of the volume of the reactor converted to residue. The results of the above four examples are tabulated below.

TABLE 1

| | EX. 1 | COMP. EX. A | EX. 2 | COMP. EX. B |
|---|---|---|---|---|
| Hydroxylamine hydrochloride (%) | 0.6 | 0 | 0.6 | 0 |
| Air Sweep (cm$^3$/min) | 0 | 0 | 0.5 | 0.5 |
| Residue/day (%) | 0.3 | 1.2 | 1.2 | gelled >20% |

COMPARATIVE EXAMPLE C

The same reactor and procedure as described in Comparative Example A were used, except that 2.225 g of cupric chloride and 6.675 g of cuprous chloride were used in place of the 8.9 g of cuprous chloride. The rate of residue formation was found to be 3.3% per day.

EXAMPLE 3

A continuous isomerization unit consisting of a nitrogen-swept 1 liter reaction flask equipped with reflux condenser, metering feed pump, cold trap, vacuum pump, thermometer, stirrer, and sample collection bottle was used. A catalyst solution was prepared by adding 37.3 ml of triethylamine hydrochloride to 820 ml of 1,4-dichlorobutene-2, heating the mixture to 60° C., and stirring for 2 hours, at which time 43 g of cuprous chloride was added and stirring was continued for an additional period of 2 hours. The catalyst was stored at −10° C. until needed. A 234.5 g sample of the catalyst solution and 0.6 g of hydroxylamine hydrochloride inhibitor were added to 390 ml of 1,4-dichlorobutene-1 heated to 95° C. in the continuous reactor. The pressure was held constant at 13.3 kPa, and sufficient heat was applied to boil 20 ml/min overhead, where the product was condensed and collected. The level was held constant in the reactor by feeding 20 ml/min of 1,4-dichlorobutene-2 to the reactor with a metering pump. The rate of residue formation was 0.3% per day.

EXAMPLE 4

A homogeneous, plant-size, liquid-phase, boiling reactor heated to 90°-110° C. was continuously fed with 1,4-dichlorobutene-2 at a rate such that the residence time was 30 min, using a cuprous chloride catalyst at a concentration of 0.5-2.25%. Hydroxylamine hydrochloride inhibitor was added periodically to maintain a concentration of 0.05-0.6%. The rate of residue formation was 0.6% per day. Considering the impossibility of complete air exclusion under the actual plant conditions, this result is considered to be very good. In the absence of inhibitor, the rate of residue formation would be about 1-2% per day.

We claim:

1. In the process for the isomerization of one of 1,4-dichlorobutene-2 and 3,4-dichlorobutene-1 into the other by heating the neat dichlorobutene to be isomerized in the presence of a cuprous compound catalyst in the absence of water and with substantial exclusion of air at a temperature at which the system is homogeneous, and removing the isomerized product from the reaction medium, the improvement comprising having present during the isomerization in the reaction medium a hydroxylamine salt in an amount of about 0.05-0.6%, based on the weight of dichlorobutene to be isomerized.

2. The process of claim 1, wherein the pressure in the isomerization reactor is about 0.5-80 kPa and the temperature is about 30°-150° C.

3. The process of claim 2 wherein the temperature is about 60°-120° C. and the pressure is about 2.5-28 kPa.

4. The process of claim 3 wherein the temperature is about 90°-115° C. and the pressure is about 9.3-24 kPa.

5. The process of claim 3 wherein the hydroxylamine salt is hydroxylamine hydrochloride.

6. The process of claim 4 wherein the hydroxylamine hydrochloride is formed in situ in the reaction medium.

7. The process of claim 1 which is run in a nitrogen atmosphere.

8. The process of claim 1 which is run as a batch process.

9. The process of claim 1 which is run as a continuous process.

10. The process of claim 1 wherein the catalyst is a complex of a cuprous salt with a quaternary ammonium salt.

11. The process of claim 10 wherein the catalyst is a complex of a quaternary ammonium chloride with cuprous chloride.

12. The process of claim 11 wherein the mole ratio of the quaternary ammonium chloride to cuprous chloride is about 0.8.

13. The process of claim 12 wherein the amount of catalyst is such that the amount of copper, calculated as cuprous chloride, is about 1.5% by weight of the dichlorobutenes present in the reactor.

* * * * *